United States Patent
Candiani et al.

(10) Patent No.: US 6,680,327 B2
(45) Date of Patent: Jan. 20, 2004

(54) CRYSTALLINE FORM VII OF CABERGOLINE

(75) Inventors: Ilaria Candiani, Busto Arsizio (IT); Raffaella Budelli, Sesto Calende (IT); Marco Pandolfi, Monza (IT); Mario Ungari, Milan (IT)

(73) Assignee: Pharmacia Italia SpA, Milan (IT)

( * ) Notice: Subject to any disclaimer, the term of this patent is extended or adjusted under 35 U.S.C. 154(b) by 0 days.

(21) Appl. No.: 10/221,165

(22) PCT Filed: Mar. 15, 2001

(86) PCT No.: PCT/EP01/02969

§ 371 (c)(1), (2), (4) Date: Sep. 18, 2002

(87) PCT Pub. No.: WO01/72746

PCT Pub. Date: Oct. 4, 2001

(65) Prior Publication Data

US 2003/0144516 A1 Jul. 31, 2003

(30) Foreign Application Priority Data

Mar. 24, 2000 (GB) .............................................. 0007309

(51) Int. Cl.⁷ ........................ A61K 31/48; C07D 457/06
(52) U.S. Cl. ............................ 514/288; 546/69; 546/67
(58) Field of Search ............................. 514/288; 546/69, 546/67

(56) References Cited

U.S. PATENT DOCUMENTS 4,526,892 A     7/1985   Salvati et al.

FOREIGN PATENT DOCUMENTS

| GB | 2 103 603 | 2/1983 | |
| WO | 99 48484 | 9/1999 | |
| WO | 99 59563 | 11/1999 | |
| WO | 01/72747 | * 10/2001 | .................. 546/69 |

OTHER PUBLICATIONS

Chemical Abstracts, vol. 122, No. 21, abstract No. 265741 May 22, 1995.

* cited by examiner

Primary Examiner—Charanjit S. Aulakh
(74) Attorney, Agent, or Firm—Akin Gump Strauss Hauer & Feld LLP; Dwayne L. Mason

(57) ABSTRACT

Crystalline form VII of cabergoline, a pharmaceutical composition containing it and a process for its preparation are disclosed. The process may comprise a slurry procedure using form I or mixture of forms I and VII of cabergoline in a solvent at a temperature above 30° C.

14 Claims, 4 Drawing Sheets

CRYSTALLINE FORM VII OF CABERGOLINE

The present invention concerns a new crystalline form of cabergoline, a pharmaceutical composition thereof and its use as therapeutically active agent, alone or in combination. Another aspect of the present invention relates to the preparation of this crystalline form. Cabergoline is an ergoline derivative interacting with D2 dopamine receptors and is endowed with different useful pharmaceutical activities and it is used in the treatment of hyperprolactinemia, central nervous system disorders (CNS) and other related diseases.

Cabergoline is the generic name of 1((6-allylergolin-8beta-yl)-carbonyl)-1-(3-dimethylaminopropyl)-3-ethylurea, described and claimed in U.S. Pat. No. 4,526,892. The synthesis of Cabergoline molecule is reported also in European. J. Med. Chem., 24,421, (1989) and in GB-2,103, 603-B.

During our work we discovered that cabergoline can exist in at least two crystalline forms under ambient conditions. One form (coded Form I) is an anhydrous not solvated form and, to our knowledge, it is the only form reported in the literature to date. Form VII is an anhydrous not solvated form too.

Thus, the present invention concerns a new polymorph (Form VII) of cabergoline and the preparation thereof. Another aspect relates to samples of cabergoline Form VII having a % polymorphic purity>90%, preferably >99%. The invention further provides a pharmaceutical composition of cabergoline Form VII and its use as therapeutic agent.

Form VII is the thermodynamically most stable polymorph in a range of temperature between +30° and +80° C. It can be readily prepared by slurry of form I or mixture of form I and VII in a solvent at a temperature over 30° C. The importance of cabergoline form VII rests primarily (but not exclusively) in thermodynamic stability.

Form VII shows advantages with respect to form I because of its greater stability.

Characterisation

X-ray powder diffraction (XRD), differential scanning calorimetry (DSC), infrared (IR) spectroscopy and solid state $^{13}$C-NMR were used to characterise the new form.

X-Ray Powder Diffraction

Powder X-ray diffraction was performed using either a Scintag X1 or X2 Advanced Diffraction System operating under Scintag DMS/NT© Ver 1.30a and 1.36b respectively, and Microsoft Windows NT 4.0™ software. The system used a copper X-ray source maintained at 45 kV and 40 mA to provide CuK$\alpha_1$ emission of 1.5406 angstroms and a solid state peltier cooled detector. Beam aperture was controlled using tube divergence and anti-scatter slits of 2 and 4 mm and detector anti-scatter and receiving slits of 0.5 and 0.3 mm width. Data were collected from 2 to 40° two-theta using a step scan of 0.03°/point with a one second/point counting time. The samples were hand ground using a pestle and mortar and packed into an aluminum sample tray with a 12 mm (diam.)×0.5 mm cavity.

DSC

Measurements of differential scanning calorimetry were obtained on a Mettler TA 4000 thermal analysis system. Approximately 8.5 mg samples were accurately weighed into a DSC Pan. The pans were hermetically sealed and a pinhole was punched into the Pan lid. The use of the pinhole allows for pressure release, but still assures that the thermal reactions proceed under controlled conditions. The samples were introduced into the DSC oven and then heated at a rate of 5° C./min, up to a final temperature of 135° C.

IR Spectroscopy

IR spectrum of cabergoline form VII was obtained on a Perkin Elmer FT-IR spectrophotometer PARAGON 1000. The sample was prepared by KBr powder technique registering the spectrum on reflectance.

Solid State $^{13}$C-NMR

Solid state $^{13}$C-NMR spectra were obtained on a MSL 300 Bruker instrument equipped with solid state facilities and variable temperature magic angle spinning probe. Cross polarisation experiments were performed by a decoupling field of 50 KHz and single pulse magic angle spinning experiments with recycle times ranging from 10 to 100 records.

The XRD, DSC, IR and NMR curves are shown in FIGS. 1–4 respectively.

The x-ray powder diffraction pattern for Form VII (FIG. 1) shows a crystalline structure with useful distinctive peaks at approximately 5.6, 8.1, 10.6 and 10.8° 2-theta. The DSC curve of Form VII (FIG. 2) exhibits a melting endotherm at approximately 121° C. The integrated melting endotherm has a heat of fusion of approximately 60 J/g.

Figure 1:
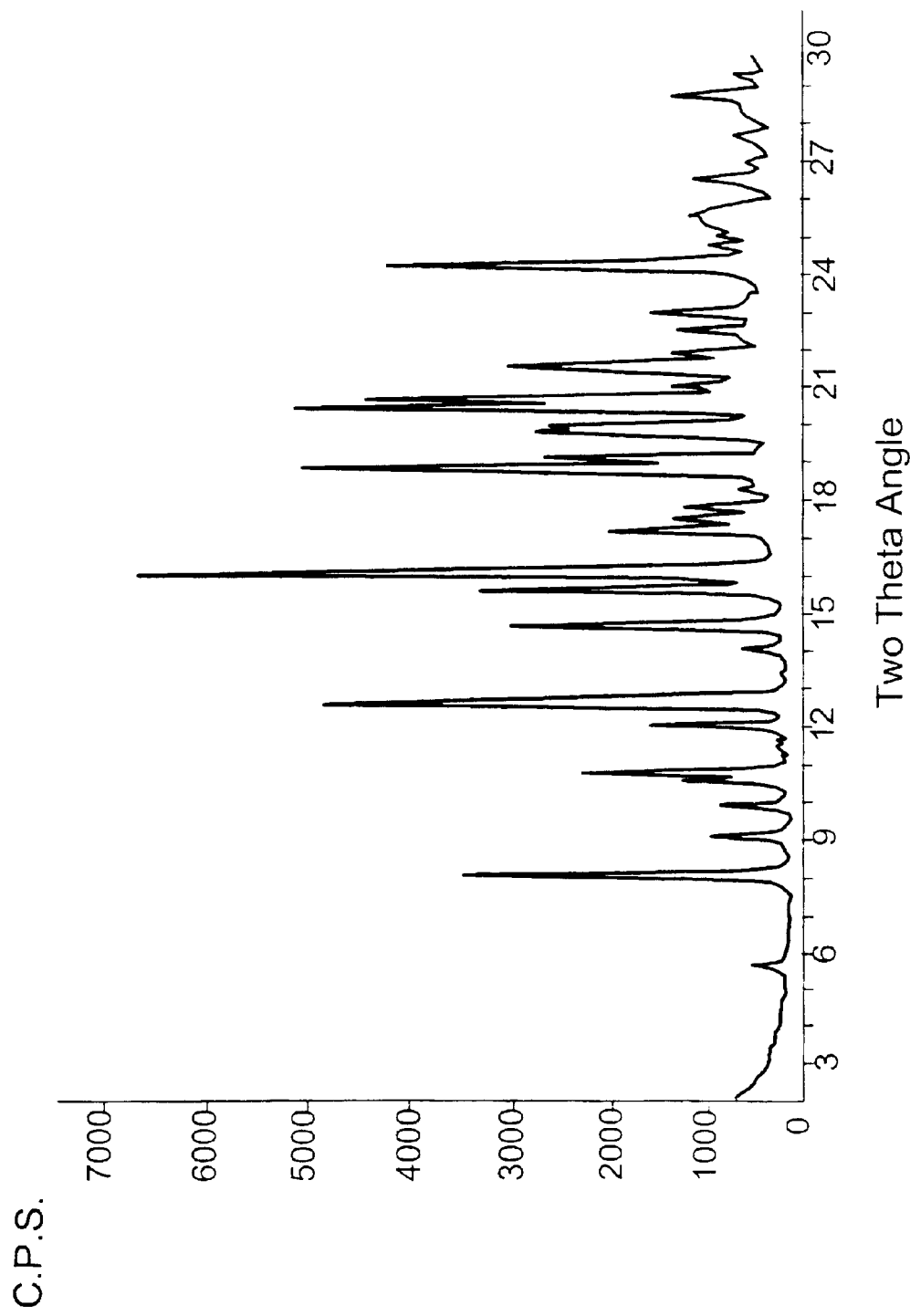
FIG. 1. XRD powder pattern of cabergoline Form VII.
Figure 2:
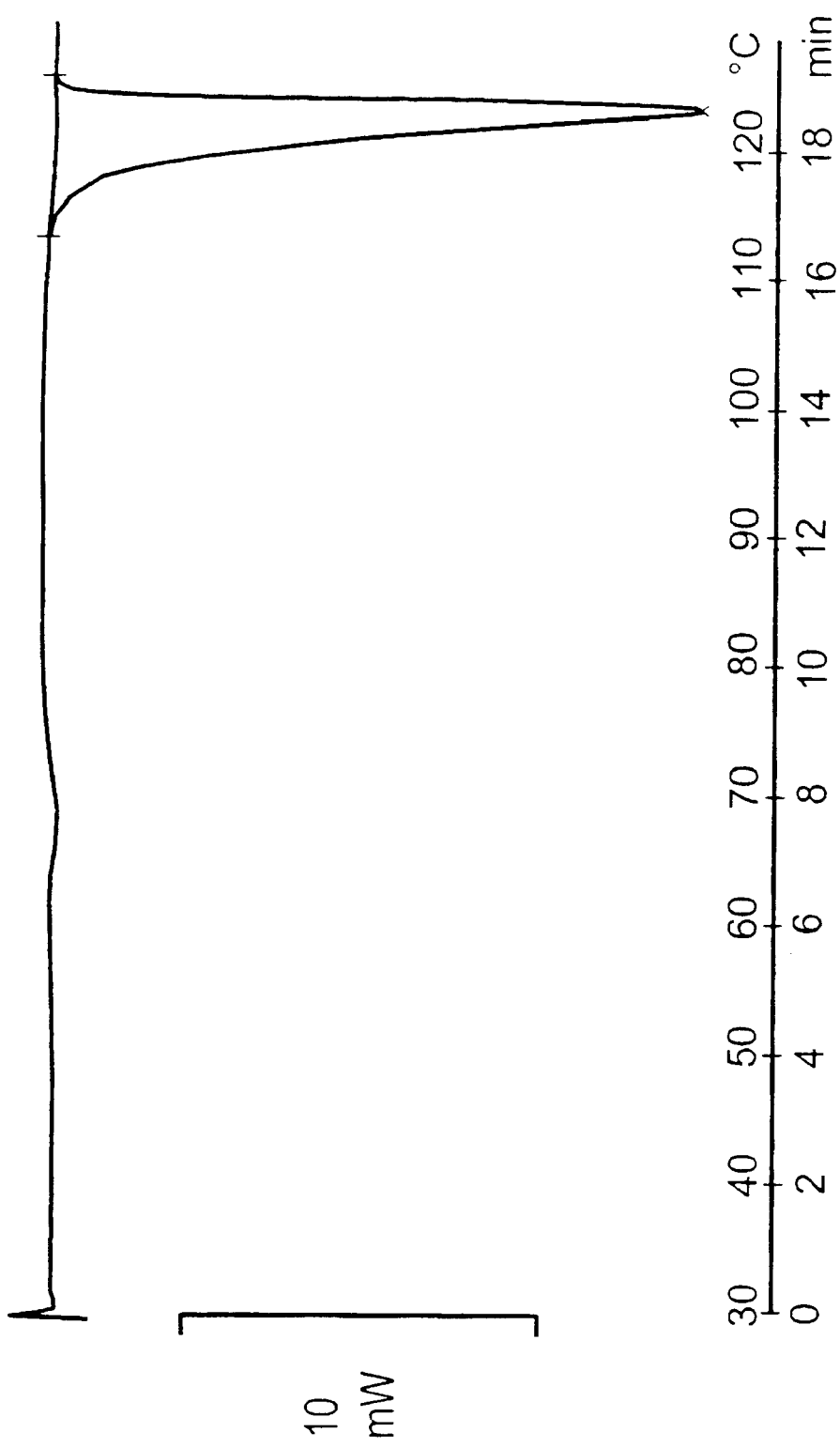
FIG. 2. DSC curve of cabergoline Form VII.
Figure 3:
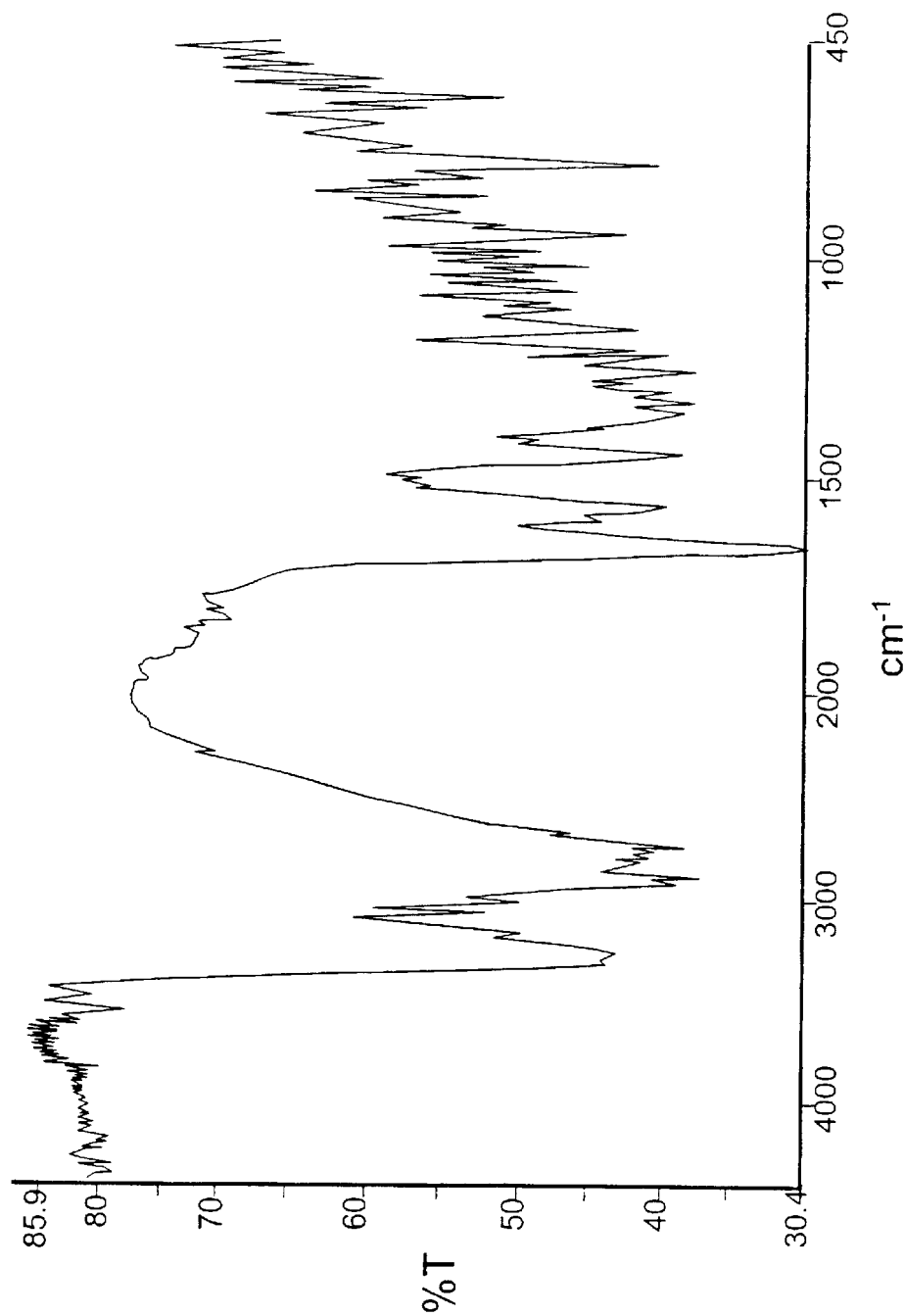
FIG. 3. IR spectrum of cabergoline Form VII (sample prepared by KBr powder technique).

The IR spectrum of Form VII is shown in FIG. 3.

Figure 4:
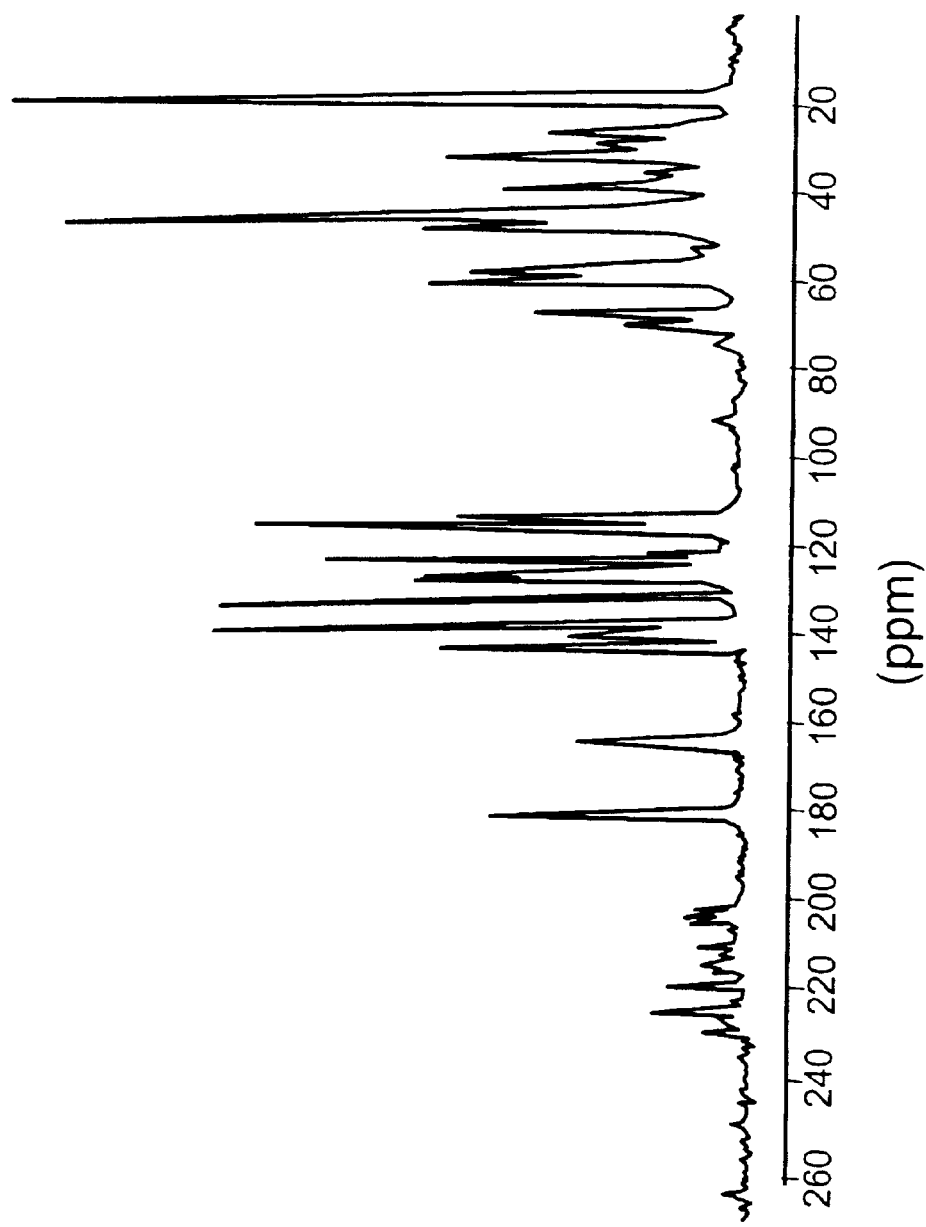
FIG. 4. Solid state $^{13}$C-NMR spectrum of cabergoline form VII.

The solid state $^{13}$C-NMR spectrum of form VII is shown in FIG. 4.

These data indicate that cabergoline Form VII is a crystalline polymorph easily distinguishable from form I by XRD, DSC and solid state $^{13}$C-NMR techniques. IR, combined with another analytical technique, is another method to distinguish the two polymorphs. The difference is a band in the region of 3500 cm$^{-1}$ that appears like a shoulder of a greater signal.

Crystalline cabergoline I has been reported in Il Farmaco, 50 (3), 175–178 (1995). However, to applicants' knowledge, no one has reported any other crystalline form.

In summary, cabergoline exists in at least two crystalline forms. Form I is a crystal (melting point=98°–105° C. by DSC, heat of fusion of _60 J/g) with a characteristic powder XRD pattern and $^{13}$C-NMR spectrum.

Form VII is a crystalline (melting point=121° C. by DSC, heat of fusion about 60 J/g) with characteristic powder XRD pattern and $^{13}$C-NMR spectrum. DSC too is very different from that of form I.

The present invention also provides a process for producing crystalline cabergoline Form VII by subjecting crystals of form I or a mixture of crystals form I and VII to a slurry procedure at a temperature over 30° C. Preferably, the process comprises suspending crystals of form I or a mixture of crystals form I and VII in an organic solvent, such as n-heptane, diethyl ether, or n-hexane, at a temperature of from +30° to +80° C., more preferably about 55° C. The resultant suspension is then stirred at this temperature for about from 24 to 120 hours, more preferably for about 48 hours.

The thus obtained crystals of Form VII may be recovered by common procedures, for example by filtration under reduced pressure or by centrifugal filtration, followed by drying the crystals, to obtain the crystalline Form VII cabergoline of the present invention. Like cabergoline Form I, Forms VII displays a significant inhibitory effect with regard prolactine and has therapeutic properties that make it possible to treat patients who have pathological conditions associated with an abnormal prolactin level, thus is useful in human and/or veterinary medicine.

Cabergoline is also active, alone or in combination, in the treatment of reversible obstructive airways diseases, for controlling intraocular pressure and for the treatment of glaucoma. It is also employed in the veterinary field, as antiprolactin agent and in cutting down drastically the proliferation of vertebrate animals. The several uses of cabergoline are for example described in WO9948484, WO9936095, U.S. Pat. No. 5,705,510, WO9505176, EP040325.

Forms VII in accordance with the invention is particularly useful in the treatment of Parkinson's disease (PD), Restless Legs Syndrome (RLS), treatment of diseases like Progressive Supranuclear Palsy (PSP) and Multysystemic atrophy (MSA). Thus, another aspect of the instant invention concerns a method for treatment of Parkinson's disease (PD), Restless Legs Syndrome (RLS), Progressive Supranuclear Palsy (PSP) and Multysystemic atrophy (MSA) which comprises administering to a host an effective amount of cabergoline Form VII.

Cabergoline Forms VII of the present invention may be used in a manner similar to that of cabergoline Form I; therefore, a person skilled in the art of CNS diseases treatment will be able to ascertain, without undue experimentation, an appropriate treatment protocol for administering a compound of the present invention. The dosage, mode and schedule of administration for compounds of this invention are not particularly restricted, and will vary with the particular compound employed. Thus Forms VII of the present invention may be administered via any suitable route of administration, preferably orally. For CNS diseases treatment, the dosage may be, for example, in the range of about 0.5 to about 50 mg/patient/day, preferably 2 to 4 mg daily as monotherapy and 2 to 6 mg daily as adjuvant therapy. The actual dose used will vary according to the particular composition formulated, the route of administration, and the particular disease being treated. Many factors that modify the action of the drug will be taken into account in determining the dosage including age, weight, sex, diet and the physical condition of the patient.

The present invention also provides pharmaceutical compositions (formulations) containing an effective amount of Form VII in combination with one or more pharmaceutically acceptable carriers, excipients, diluents or adjuvants.

For example, Form VII invention may be formulated in the form of tablets, pills, powder mixtures, capsules, injectables, solutions, suspensions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration as a suspension (microdispersion) or in solution. Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

Example 1

55.5 g of crystalline cabergoline form I were added to 700 ml of n-heptane at 55° C. The suspension was stirred at this temperature for about 48 hours and then filtered using a glass filter under vacuum. The resulting crystals were dried under vacuum at 40° C. for 24 hours. After drying the resultant crystal form VII was identified by XRD, DSC, IR and NMR, data shown in FIGS. 1–4 respectively, having polymorphic purity>99%.

Example 2

27.65 g of cabergoline were dissolved in 1,4-dioxane at 40° C.; the final solution (68 mL) was slowly cooled till to −5° C., in stirring. After 24 hours the obtained solid was filtered on sintered-glass G4 filter and then dried at from 30° C. to 65° C. under $N_2$ and vacuum. The resultant crystals form VII were identified by DSC and IR. Yield was 45.2%.

What is claimed is:

1. Crystalline form VII of cabergoline.
2. Crystalline form VII of cabergoline according to claim 1 which is anhydrous, non-solvated and has a percentage purity greater than 92%.
3. Crystalline form VII of cabergoline according to claim 1 which is anhydrous, non-solvated and has a percentage purity greater than 99%.
4. Crystalline form VII of cabergoline according to claim 1 having the XRD powder pattern of FIG. 1.
5. A pharmaceutical composition which comprises an effective amount of crystalline Form VII, as defined in claim 1 in combination with one or more pharmaceutically acceptable carriers, excipients, diluents or adjuvants.
6. A process for producing cabergoline Form VII as defined in claim 1, which process comprises subjecting crystals of form I, or a mixture of forms I and VII, of cabergoline to a slurry procedure at a temperature above 30° C., followed by recovery and drying of the resulting crystals.
7. A process according to claim 6 in which the slurry procedure comprises suspending crystals of form I or a mixture of forms I and VII of cabergoline in an organic solvent, at a temperature of from +30° to +80° C., and stirring the resultant suspension for from 24 to 120 hours.
8. A process according to claim 7 in which the solvent is diethyl ether, n-heptane or n-hexane.
9. A pharmaceutical composition which comprises an effective amount of crystalline Form VII, as defined in claim 2 in combination with one or more pharmaceutically acceptable carriers, excipients, diluents or adjuvants.
10. A pharmaceutical composition which comprises an effective amount of crystalline Form VII, as defined in claim 3 in combination with one or more pharmaceutically acceptable carriers, excipients, diluents or adjuvants.
11. A pharmaceutical composition which comprises an effective amount of crystalline Form VII, as defined in claim 4 in combination with one or more pharmaceutically acceptable carriers, excipients, diluents or adjuvants.
12. A process for producing cabergoline Form VII as defined in claim 2, which process comprises subjecting crystals of form I, or a mixture of forms I and VII, of cabergoline to a slurry procedure at a temperature above 30° C., followed by recovery and drying of the resulting crystals.

13. A process for producing cabergoline Form VII as defined in claim 3, which process comprises subjecting crystals of form I, or a mixture of forms I and VII, of cabergoline to a slurry procedure at a temperature above 30° C., followed by recovery and drying of the resulting crystals.

14. A process for producing cabergoline Form VII as defined in claim 4, which process comprises subjecting crystals of form I, or a mixture of forms I and VII, of cabergoline to a slurry procedure at a temperature above 30° C., followed by recovery and drying of the resulting crystals.

* * * * *